US005530129A

United States Patent [19]

Gallenkamp et al.

[11] Patent Number: 5,530,129

[45] Date of Patent: Jun. 25, 1996

[54] PROCESS FOR THE PREPARATION OF 1,2,4-TRIAZINE-3,5-DIONES

[75] Inventors: Bernd Gallenkamp, Wuppertal; Werner Hallenbach, Monheim; Lothar Rohe, Wuppertal, all of Germany

[73] Assignee: Bayer Aktiengesellschaft, Leverkusen, Germany

[21] Appl. No.: 508,639

[22] Filed: Jul. 28, 1995

[30] Foreign Application Priority Data

Aug. 4, 1994 [DE] Germany .......................... 44 27 529.3

[51] Int. Cl.$^{6}$ ................................................ C07D 253/075

[52] U.S. Cl. ................................................ 544/182

[58] Field of Search ................................................ 544/182

[56] References Cited

U.S. PATENT DOCUMENTS 3,883,528 5/1975 Mylari .................................... 260/248

3,905,971 9/1975 Miller .................................... 260/248

4,198,407 4/1980 Rösner et al. .......................... 544/182

FOREIGN PATENT DOCUMENTS 0330041 8/1989 European Pat. Off. .

2230454 1/1973 Germany .

2722537 11/1978 Germany .

OTHER PUBLICATIONS

F. Yoneda, et al., J. Heterocyclic Chem., vol. 17, pp. 1365–1368, (1980).

Abstract of EP 33 041, (Aug. 5, 1981).

*Primary Examiner*—John M. Ford

*Attorney, Agent, or Firm*—Sprung Horn Kramer & Woods

[57] ABSTRACT

The invention relates to a novel process for the preparation of 1,2,4-triazine-3,5-diones by decarboxylation of corresponding 6-carboxy-1,2,4-triazine-3,5-diones, characterized in that it is carried out in aprotic organic solvents.

5 Claims, No Drawings

PROCESS FOR THE PREPARATION OF 1,2,4-TRIAZINE-3,5-DIONES

The invention relates to a novel process for the preparation of 1,2,4-triazine-3,5-diones.

It is known that 1,2,4-triazine-3,5-diones can be prepared by decarboxylation of corresponding 6-carboxy-1,2,4-triazine-3,5-diones (cf. DE-A-2423972; DE-A- 2722537, EP-A 330041; J. Heterocycl. Chem. 17 (1980), 1365–1368).

In these processes, in general, use is made of solvents having very high boiling points, for example diphenyl ethers and/or of substances which may have a catalytic action, for example thiourea or mercapto acetic acid. In many cases the decarboxylation products are obtained in unsatisfactory quality, with a particular problem being caused by the separation of solvent and unwanted decomposition products. If the decarboxylation is carried out without solvent, the products are obtained in a form in which they are difficult to process.

It has now been found that 1,2,4-triazine diones of the general formula (I)

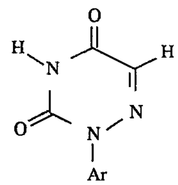

(I)

in which

Ar represents in each case optionally substituted aryl or heteroaryl, are obtained in good yields and in high purity if 6-carboxy-1,2,4-triazine diones of the general formula (II)

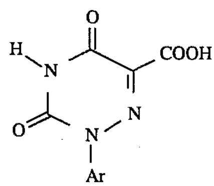

(II)

in which

Ar is as defined above are reacted in aprotic organic solvents—without further additives—having boiling points of between 50° C. and 150° C., at temperatures of between 80° C. and 220° C. and, if desired, under elevated pressure.

Surprisingly, it is possible to obtain the 1,2,4-triazine-3,5-diones of the general formula (I) in a smooth reaction in good yields and in high purity by the process according to the invention, while avoiding the abovementioned disadvantages of the known preparation methods.

When the process according to the invention is carried out under elevated pressure, relatively low-boiling solvents can also be used. This reduces the thermal stress on the starting material and product and simplifies the working-up operation (with distillative recovery of the solvent).

The process according to the invention thus constitutes a valuable enrichment of the art.

The process according to the invention relates preferably to the preparation of compounds of the formula (I), in which Ar represents in each case optionally substituted phenyl, naphthyl, pyridyl, pyrimidyl, pyrazinyl, pyridazinyl or triazinyl, the possible substituents preferably being selected from the series consisting of halogen, hydroxyl, amino, formyl, cyano, nitro, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl, $C_1$–$C_4$-alkylamino, di-($C_1$–$C_4$-alkyl)amino, $C_1$–$C_4$-alkylcarbonyl, $C_1$–$C_4$-alkoxy carbonyl, phenyl, phenoxy, phenylthio, phenylsulphinyl, phenylsulphonyl, phenylamino, phenylcarbonyl, phenylhydroxymethyl, phenylcyanomethyl, phenyl-$C_1$–$C_4$-alkyl, pyridyl, pyrimidinyl, pyridyloxy, pyrimidyloxy, pyridylthio, pyrimidylthio, pyridylamino, pyrimidylamino (in which the phenyl, pyridyl or pyrimidyl groups are in each case optionally substituted by halogen, hydroxyl, amino, formyl, cyano, nitro, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl $C_1$–$C_4$-halogenoalkylsulphonyl, $C_1$–$C_4$-alkylamino, di-($C_1$–$C_4$-alkyl)amino, $C_1$–$C_4$-alkylcarbonyl and/or $C_1$–$C_4$-alkoxy-carbonyl).

The invention relates in particular to the preparation of compounds of the formula (I) in which Ar represents optionally substituted phenyl, the possible substituents preferably being selected from the series consisting of fluorine, chlorine, bromine, hydroxyl, amino, formyl, cyano, nitro, methyl, ethyl, n- or iso-propyl, n-, iso-, s- or t-butyl, trifluoromethyl, methoxy, ethoxy, difluoromethoxy, trifluoromethoxy, methylthio, ethylthio, trifluoromethylthio, methylsulphinyl, ethylsulphinyl, trifluoromethylsulphinyl, methylsulphonyl, ethylsulphonyl, trifluoromethylsulphonyl, methylamino, ethylamino, dimethylamino, acetyl, propionyl, methoxycarbonyl, ethoxycarbonyl, phenyl, phenoxy, phenylthio, phenylsulphinyl, phenylsulphonyl, phenylamino, phenylcarbonyl, phenylhydroxymethyl, phenyl-cyanomethyl, benzyl, pyridyl, pyrimidyl, pyridyloxy, pyrimidyloxy, pyridylthio, pyrimidylthio, pyridylamino or pyrimidylamino (in which the phenyl, pyridyl or pyrimidyl groups are in each case optionally substituted by fluorine, chlorine, bromine, hydroxyl, amino, formyl, cyano, nitro, methyl, ethyl, n- or iso-propyl, n-, iso-, s- t-butyl, trifluoromethyl, methoxy, ethoxy, difluoromethoxy, trifluoromethoxy, methylthio, ethylthio, trifluoromethylthio, methylsulphinyl, ethylsulphinyl, trifluoromethylsulphinyl, methylsulphonyl, ethylsulphonyl, trifluoromethylsulphonyl, methylamino, ethylamino, dimethylamino, acetyl, propionyl, methoxycarbonyl and/or ethoxycarbonyl).

Using, for example, 6-carboxy-2-(4-hydroxy-3-methylphenyl)-1,2,4-triazine-3,5(2H,4H)-dione as starting compound, the course of the reaction in the process according to the invention can be illustrated by the following formula scheme:

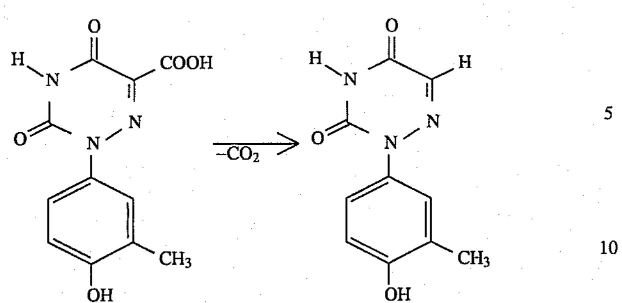

A general definition of the 6-carboxy-1,2,4-triazinediones to be used as starting materials in the process according to the invention for the preparation of the compounds of the general formula (I) is given by the formula (II). In the formula (II) Ar preferably or in particular has that meaning which has already been indicated above, in connection with the description of the compounds of the formula (I), as being preferable or particularly preferable for Ar.

The starting materials of the formula (II) are known and/or can be prepared by processes which are known per se (cf. DE-A 2423972; DE-A 2722537; EP-A 330041; J. Heterocycl. Chem. 17 (1980), 1365–1368).

The process according to the invention is carried out using one or more aprotic organic solvents. These include, in particular, aliphatic, alicyclic or aromatic, optionally halogenated, hydrocarbons such as, for example, benzene, toluene, xylene, chlorobenzene, hexane, cyclohexane, chloroform; ethers such as diisopropyl ether, t-butyl methyl ether, t-amyl methyl ether, dioxane, tetrahydrofuran or ethylene glycol dimethyl or diethyl ether; ketones such as acetone, butanone, methyl isopropyl ketone or methyl isobutyl ketone; nitriles such as acetonitrile, propionitrile or butyronitrile; and esters such as methyl acetate, ethyl acetate, n- or isopropyl acetate and n-, iso-, s- or t-butyl acetate.

Preferred solvents for the process according to the invention and which may be mentioned are ethers such as ethylene glycol dimethyl ether and t-amyl methyl ether.

When carrying out the process according to the invention the reaction temperatures can be varied within a relatively wide range. The process is in general carried out at temperatures of between 80° C. and 220° C., preferably at temperatures of between 150° C. and 200° C.

The process according to the invention is preferably carried out under elevated pressure. It is preferred to work in the pressure range between 1 and 100 bar, in particular between 2 and 50 bar.

In a preferred embodiment of the process according to the invention, the 6-carboxy-1,2,4-triazinedione of the formula (II) is suspended in an aprotic organic solvent and is stirred in an autoclave, at the temperature which is required for decarboxylation, until the end of the reaction.

The reaction product can be worked up and isolated in a conventional manner. For example, the mixture is filtered with suction and the solvent is carefully distilled off under reduced pressure from the filtrate. The product which remains as residue, of the formula (I), can generally be reacted further without additional purification.

The compounds of the formula (I) to be prepared by the process according to the invention may be employed as intermediates for the preparation of compounds which have an endoparasiticidal action (cf. EP-A 330041).

PREPARATION EXAMPLES

Example 1

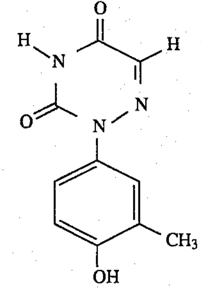

144.8 g (517 mmol) of 6-carboxy-2-(4-hydroxy-3-methylphenyl)-1,2,4-triazine- 3,5(2H,4H)-dione are suspended in 870 ml of ethylene glycol dimethyl ether and the mixture is stirred in a sealed autoclave at 200° C. for 3 hours. After the autoclave has been cooled and opened, the mixture is filtered with suction and the solvent is carefully distilled off under reduced pressure from the filtrate.

118.1 g (purity: 79.3%, i.e. yield: 82.6% of theory) are obtained of 2-(4-hydroxy-3-methylphenyl)- 1,2,4-triazine-3,5(2H,4H)-dione.

We claim:

1. In the heating of 6-carboxy-1,2,4-triazinediones of the formula

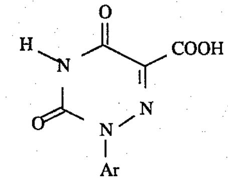

in which

Ar is optionally substituted aryl or heteroaryl, in an organic solvent to effect decarboxylation thereof to produce a 1,2,4-triazine-3,5-dione of the formula

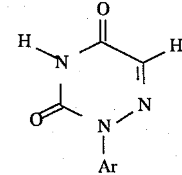

the improvement which comprises effecting the decarboxylation at a temperature from 80° to 220° C. in an aprotic organic solvent having a boiling point from 50° to 150° C.

2. The process according to claim 1, wherein the decarboxylation is effected under elevated pressure.

3. The process according to claim 1, wherein the solvent is selected from the group consisting of an optionally halogenated aliphatic, alicyclic or aromatic hydrocarbon, an ether, a ketone, a nitrile and an ester.

4. The process according to claim 1, wherein the solvent is selected from the group consisting of benzene, toluene, xylene, chlorobenzene, hexane, cyclohexane, chloroform, diisopropyl ether, t-butyl methyl ether, t-amyl methyl ether, dioxane, tetrahydrofuran, ethylene glycol dimethyl or diethyl ether, acetone, butanone, methyl isopropyl ketone, methyl isobutyl ketone, acetonitrile, propionitrile, butyronitrile, methyl acetate, ethyl acetate, n- or isopropyl acetate and n-, iso-, s- or t-butyl acetate.

5. The process according to claim 1, wherein the solvent is t-butyl methyl ether, t-amyl methyl ether, dioxane, tetrahydrofuran, ethylene glycol dimethyl or diethyl ether, acetone, butanone, methyl isopropyl ketone, methyl isobutyl ketone, acetonitrile, propionitrile, butyronitrile, methyl acetate, ethyl acetate, n- or isopropyl acetate and n-, iso-, s- or t-butyl acetate.

* * * * *